(12) United States Patent
Narayanaswamy et al.

(10) Patent No.: US 9,629,536 B2
(45) Date of Patent: Apr. 25, 2017

(54) ILLUMINATION SYSTEM FOR OPTHALMIC MICROSCOPE, AND ITS OPERATION METHOD

(75) Inventors: Ravilla Kasthuri Narayanaswamy, Chennai (IN); Parameswaran Subash, Chennai (IN); Chamsoudine Mohamed Ittaythula, Puducherry (IN); Abimanyu Jayaram, Chennai (IN); Thirugnanasambantham Verra Soundra Senthil Murugan, Chennai (IN)

(73) Assignee: M/s. Appasamy Associates, Chennai, Tamil Nadu (IN)

( * ) Notice: Subject to any disclaimer, the term of this patent is extended or adjusted under 35 U.S.C. 154(b) by 230 days.

(21) Appl. No.: 14/115,693

(22) PCT Filed: May 4, 2012

(86) PCT No.: PCT/IN2012/000333
§ 371 (c)(1),
(2), (4) Date: Nov. 5, 2013

(87) PCT Pub. No.: WO2012/150613
PCT Pub. Date: Nov. 8, 2012

(65) Prior Publication Data
US 2014/0092362 A1 Apr. 3, 2014

(30) Foreign Application Priority Data
May 5, 2011 (IN) ............................ 1571/CHE/2011

(51) Int. Cl.
*A61B 3/10* (2006.01)
*A61B 3/00* (2006.01)
(Continued)

(52) U.S. Cl.
CPC .............. *A61B 3/0008* (2013.01); *A61B 3/13* (2013.01); *G02B 21/0012* (2013.01); *G02B 21/06* (2013.01); *G02B 27/14* (2013.01)

(58) Field of Classification Search
USPC .................................................. 351/221, 246
See application file for complete search history.

(56) References Cited

U.S. PATENT DOCUMENTS 5,760,952 A 6/1998 Koetke
5,790,306 A 8/1998 Klienberg et al.
(Continued)

FOREIGN PATENT DOCUMENTS

DE 196 50 773 7/1997

*Primary Examiner* — Jack Dinh
(74) *Attorney, Agent, or Firm* — Hamre, Schumann, Mueller & Larson, P.C.

(57) ABSTRACT

The present invention discloses a illumination system for ophthalmic microscope and its operation method. Light beams generated by White LED, passes through the condenser and relay system to produce illumination on retina of the eye and boundary of the illumination is determined by the aperture stop. To enhance the visualization of red glow, a Single source beam then divided into two beams using divider system contains Beam splitter and mirror. Transmitted beams and reflected beams are made to focus on circular areas coated with reflective material of virtual beam splitter which is positioned coaxially with observation system of the microscope. Focused beam then passes through the objective lens of the microscopic system. Reflected beams from retina then passes through the objective lens and reaches the observation system via Virtual Beam Splitter.

10 Claims, 5 Drawing Sheets

(51) Int. Cl.
*A61B 3/13* (2006.01)
*G02B 21/06* (2006.01)
*G02B 21/00* (2006.01)
*G02B 27/14* (2006.01)

(56) References Cited

U.S. PATENT DOCUMENTS

| | | |
|---|---|---|
| 7,307,785 B2 | 12/2007 | Obrebski et al. |
| 7,697,199 B2 | 4/2010 | Reimer et al. |
| 7,907,336 B2 | 3/2011 | Abele et al. |
| 2004/0227989 A1 | 11/2004 | Obrebski et al. |
| 2005/0288745 A1 | 12/2005 | Andersen et al. |
| 2007/0258045 A1 | 11/2007 | Yamaguchi et al. |
| 2011/0007274 A1 | 1/2011 | Ono et al. |
| 2011/0037947 A1 | 2/2011 | Reimer et al. |
| 2011/0037948 A1 | 2/2011 | Horvathe et al. |
| 2011/0038040 A1 | 2/2011 | Abele et al. |

ILLUMINATION SYSTEM FOR OPTHALMIC MICROSCOPE, AND ITS OPERATION METHOD

FIELD OF THE INVENTION

The present invention relates to eye surgery. More particularly, the present invention relates to a illumination system for Ophthalmic Microscope, and its operation method deployed in eye surgery, with particular focus to cataract surgery, the said illumination system being employed in enhancing the "red reflex" glow thereby increasing the surgical efficiency, so as to enable replacing natural eye lens with intra-ocular artificial lens in the context of cataract surgery.

BACKGROUND OF THE INVENTION

In the present day scenario, it is observed that due to better medical facilities and better living conditions, the life span of the human population worldwide, has increased. Therefore, the average age of the human population worldwide is also on the rise. Even though the rising average age of the population is a positive development, however, it is also observed that with aging, certain health problems occur in the human body, in the natural scheme of things. Such health problems are inclusive of, but not restricted to, eye disorders. The human eye is an intricate and a very crucial organ. In this context, it is observed that, if there is a deterioration in the functioning of the eye, it can be very debilitating for an aging individual to conduct their day-to-day activities.

The deterioration in the functioning of the human eye can be due to a variety of eye disorders. Some of the commonly occurring eye disorders are inclusive of, but not restricted to, astigmatism, diabetic retinopathy, presbyopia, cataract, nystagmus, Keratoconus glaucoma and macular degeneration. The reasons for the occurrence of the eye disorders could be as wide as the range of the eye disorders. There may be different reasons for onset of the eye diseases. Aging, injury or damages to the eye parts may be the most prominent reasons. Some chronic diseases, including diabetes may cause eye troubles as well. Lack of vitamins can also contribute to eye diseases.

Regular usage of computers without keeping minimum distance, cell phones, video games, laptops, and watching high definition television with improper light source can also be treated as possible causes of eye disease. Today in modem times we rely on sophisticated technical gadgets to ease our work and unknowingly we suffer from eye fatigue or strain in eye muscles. This may also lead to permanent vision loss or temporary blindness. Anxiety, allergies and genetic factors are also responsible causes of eye disease. Environmental conditions like dry air or wind, dusty atmosphere and smoke also provokes eye problems.

In this context, in addition, it is also observed that, even though, the reasons for the occurrence of the eye disorders may be as wide as the range of the eye disorders, there are some predominant reasons inclusive of, but not restricted to, aging. It is also to be noted that, aging is not the only reason for the occurrence of all eye disorders, however, some of the eye disorders, like cataract, for instance, are predominantly attributable to ageing.

In this context, it would be pertinent to describe the internal structure of the eye. As it is already known, the eye is in itself, an intricate and a very crucial organ. A detailed examination of the internal structure of the human eye reveals that, the human eye is a ball-shaped structure. The human eye is inclusive of the following parts: The Sclerotic is the outer coating of the eye, which is white in color, protects the interior of the eye and also provides shape to the eye; the Cornea is the front part of the Sclerotic and is transparent to light, and also light coming from an object enters the eye through Cornea. The Iris is at the back of the Cornea. It is to be noted that, the eye lens is a double convex lens with the help of which image is formed at the retina by refraction of light. Space between cornea and eye lens is filled with a transparent fluid, called aqueous humor. Space between the eye lens and retina is filled with a jelly-like transparent fluid, called vitreous humor. Retina serves the purpose of a screen in the eye. Images of the object(s) are formed on the retina. Retina is at the back of the eye lens. It is well known to ophthalmic professionals that, "cataract" is an eye disorder which primary affects the eye lens. In medical terminology, the lens of the human eye is said to be afflicted with "cataract" when the lens of the eye, which is naturally transparent, becomes opaque, causing a progressive, painless loss of vision. The symptoms through which, cataract is recognizable are, in general, vision may be blurred, contrast may be lost, and halos may be visible around lights. The only treatment that provides a cure for "cataracts" is surgery. Occasionally, cataracts cause changes (such as swelling of the cataract or glaucoma) that lead doctors to recommend that, the cataract be removed quickly.

Conventionally, Phacoemulsification procedure is used for performing cataract surgeries. Phacoemulsification is a procedure in which the lens clouded by a cataract is broken up by ultrasound, irrigated, and suctioned out. It is known that, eye surgery is an intricate procedure, which requires a lot of meticulousness and attention, while the surgery is under progress, and also, in terms of post-operative care. However, it is also pertinent to note that, if the surgery is performed in an efficient manner, the outcome of the surgery is excellent, and the expected results are achieved. The excellent outcome of the surgery lies not merely in the dexterity of the eye surgeon, but also, in the instrumentation and medication deployed, for conducting the surgery. The said instrumentation includes, but is not limited to, the surgical tools such as, forceps, hooks, speculum, microscope, retinoscope, refraction box and the like, that are employed for conducting the surgery. Since, the eye is a fragile organ and any surgery involves observing the eye under a microscope, and concurrently performing the surgery in conjunction with an illumination system.

In this context it is pertinent to observe that, various types of operating microscopes are used for cataract surgery. With respect to the cataract operation conducted now, the conventional phacoemulsification process comprises irrigation and suction. The suction technique is a method of cutting the front capsule of a crystalline lens along the contour thereof, inserting a suction device from the cut edge, sucking the content of the whitish crystalline lens, and implanting an Inter ocular lens (IOL) therein in place of the sucked content.

When the suction technique is performed, an operating microscope is used for observation of the enlarged view of an eye to be operated. At this time of operation in order to improve the visualization, an image of Transillumination produced by the scattering and reflections from the retina of the eye is widely utilized. In particular, when the position of the cut edge in the front capsule is checked in order to insert the suction device and when it is determined whether or not the content of the crystalline lens is completely sucked, the red reflex is extremely effective. In such a scenario, it is also pertinent to note that, the illumination system employed is also a crucial component that is involved in the outcome of the surgery and hence, the outcome of the surgery depends to a certain degree, on the functioning of the illumination system. The efficiency of functioning of the illumination system includes, but is not restricted to, the lighting provided to illuminate the eye lens. The illumination system provides lighting, which is termed as "red reflex" and plays a major role in illuminating the natural eye lens, for the purpose of removal of the existing natural lens, and inserting the artificial intraocular lens. There are certain ancillary components also, for instance, the stable positioning of microscope employed for conducting the surgery. Even though, such ancillary components may seem insignificant, however, it is pertinent to note that, these components may play a small but significant role in increasing the excellence of the outcome of the eye surgery.

In order to obtain the red reflex suitable for an operator, various units have been proposed and executed up to now. As main examples of such units, there are "a Zero degree Illumination unit, in which a deflection mirror is disposed between the right and left observation optical axis of an objective lens and a complete co-axial illumination unit in which an illumination optical axis and observation optical axis is aligned with each other using a half mirror. However, in the zero degree illumination unit a region of red reflex resulting from an observation light flux in the right is different from that in the left. Therefore when the binocular vision is conducted, there is a problem in which good fusion of the image is not obtained. In addition, in the complete co axial illumination unit, because of a reduction in amount of observation light flux resulting from the use of the half mirror, only an entirely dark observation image can be obtained. Therefore, there is a problem in which the visibility is inferior.

An operating Microscope includes an Oblique mirror which deflects the emitted light from the source with an angle towards an eye to be operated. The angled illumination unit is generally constructed such that an angle of 2 deg for obtaining the red reflex and an oblique angle of 6 degree for obtaining a shadow contrast can be realized. The oblique angle particularly for obtaining the red reflex is within a range of about +/−0.5 deg is the condition following in other operating microscopes in market. In the illumination at such an angle is called "approximately coaxial illumination". In the operation microscope using the angled illumination unit the following problems emerges, i.e., because an angle is provided between the illumination and the observation optical axis a region which is not irradiated with the illumination light is caused within the observable area of the retina and the part of the red reflex is not incident into the observation optical system. As a result a region in which the red reflex is not obtained is caused within an observation image.

Certain proposals are known in the art, which are directed towards similar application(s).

U.S. Pat. No. 5,790,306 titled Microscope beamsplitter, reveals a zonal beam splitter in the optical signal path for splitting the optical signal. The beam splitter comprises two right-angular prisms. A reflective element that occludes a portion of the optical path and reflects a portion of the optical signal path.

U.S. Pat. No. 7,907,336 titled Surgical microscope having an illuminating arrangement reveals an illuminating arrangement configured with illuminating light from one illuminating beam path, an illuminating spot/two illuminating spots can be generated on the retina of an ideal patient eye with said illuminating spot having a diameter lying in a range of 0.5 mm to 1.5 mm. Also, an illuminated field diaphragm is mounted to differentiate the optic images of one image plane from another.

U.S. 20110038040 titled Surgical microscope having an illuminating arrangement reveals a surgical microscope which is designed as an ophthalmologic surgical microscope. This surgical microscope has an illuminating arrangement with which an illuminating beam path can be adjusted with the illuminating beam path running coaxially to the stereoscopic viewing beam path. The Illuminating beam path is guided through the microscope main objective to the object region. For the purpose, a beam deflection unit is provided for the surgical microscope which is configures as a beam splitter. Preferably, the light exit section is the end of a light conductor. The Light exit section can, however, also be configured as a light source such as a light emitting diode, xenon lamp or a halogen lamp.

U.S. 20040227989 titled Microscopy system for eye surgery and method of illumination reveals a microscopy system, wherein the retro illumination system comprises a light source for generating of a light beam and a beam splitter for splitting the light beam into a beam of standard illumination light and the beam of retro illumination light such that the beam of standard illumination light is directed towards the object plane from the object lens side of the object plane, and wherein an angle between a main ray of the beam of retro illumination light and a main ray of the beam of standard illumination light is greater than 30.

U.S. Pat. No. 7,697,199 titled Lighting device and observation device reveals a lighting device described for an observation device, in particular for an ophthalmologic operating microscope, as well as such an observation device. The lighting device has a light source as well as a number of optical components, which are provided between light source and an objective element. The optical components are designed according to the invention in such a way that the imaging of the lighting pupil and the observation pupils is produced on the fundus of the eye.

U.S. 20110037947 titled Illumination device as well as observation device discloses an illumination device for an observation device comprising one, two or more observation beam paths with one respective beam of observation rays, especially for an ophthalmologic surgical microscope, and a corresponding observation device. Said illumination device is provided with at least one light source for generating at least one beam of observation rays in order to illuminate an object that is to be observed. According to one embodiment of the invention, at least two partial bundles of illumination rays are provided, each of which extends coaxial to a corresponding beam of observation rays, while the partial beams of illumination rays are embodied so as to form two or several illumination spots on the fundus of an object that is to be observed, e.g. an eye, said illumination spots having variable sizes, thus allowing the illumination beam to cooperate in a precisely defined manner with the observation beam paths, which makes it possible to meet especially the practical requirements regarding homogeneity of the red reflex.

DE 19650773 titled Illuminator for microscope for eye surgery esp. cataract operations reveals an illuminator having one deflector for the light arranged between the light source and the observation radiation path of the microscope. A second deflector device is also provided for the first light and is arranged closer to the observation radiation path than the first such device. The first deflector device comprises two components, of which one is fixed and the other is movable. The deflector component closest to the observation object is also provided with a deflector device on its side turned away from the light source, so that from this side the or a part of the light reflected in the direction of the observation object from the second deflector component is guided in the direction of the further deflector device.

U.S. 20110037948 titled White light emitting diode (LED) illuminator for ophthalmic endoillumination reveals an ophthalmic endoilluminator which includes one or more white light emitting diodes (LEDs), an additional light source, a first optical assembly, an optical coupling element, and an optical fiber optically coupled to the optical coupling element. The white LED is capped with a phosphor layer. The additional light source illuminates at least a portion of an exterior surface of the phosphor layer within an absorption band of phosphor material of the phosphor layer in order to excite the phosphor layer and produce additional white light. The first optical assembly receives and substantially collimates the white light. The optical coupling element receives the substantially collimated white light from the first optical assembly and directs the light to an optical fiber. The optical fiber is then used to conduct the white light into an eye.

U.S. Pat. No. 7,307,785 titled Lighting device and observation device reveals a microscopy system for eye surgery with an objective lens is suggested, which provides a retroillumination system to generate a so-called red reflex illumination during an eye-surgical treatment, in particular, during a cataract operation.

It is observed that, the known proposals do not solve requirement(s), which are specific to increasing the excellence of the outcome of the eye surgery, and thereby reduce the probability of post-operative problems for the patients as well as for the ophthalmic professionals.

Further, there is a problem in the available state of the art that the light source used generates heat in addition to light and is not efficient as a result. In the case of eye surgery, heat generated by the light source may not only mean mere wastage of energy but is also detrimental to the outcome of the surgery since the human eye is a delicate organ and excessive heat energy being present in the vicinity of the eye may have detrimental effect on the eye, while it is being operated on and also in the post-operative stage.

There is still the problem that the light source used in the illumination system generates light of wavelengths, which are very much outside the visible spectrum, like ultraviolet rays and infrared rays. Since production of such rays is detrimental to the eye an additional light filter component is deployed. This additional component means that cost and maintenance of the illumination system is increased.

There is still the problem that usage of a beam splitter component causes generation of secondary reflections. Such an optical defect decreases the efficiency and is detrimental to the overall outcome of the eye surgery since the surgeon is likely to be distracted.

There is still the problem that the mechanical components deployed for stability of the microscope are not robust. Therefore the overall outcome of the surgery may not be as desired.

In the described context, it will be amply clear to a person skilled in the art that in view of the above-mentioned problems there is a need in the art for an illumination system in which the characteristics of the light source used is not detrimental to the excellent outcome of the surgery since the human eye is a delicate organ and is susceptible to heat, and therefore excessive heat generated by the light source in the vicinity of the eye may have detrimental effect on the delicate internal structure of the eye, while it is being operated on and also afterward in the post-surgical stage.

It will also be amply clear to a person skilled in the art that in view of the above-mentioned problems there is a need in the art for an illumination system in which the wavelength characteristics of the light source used in the illumination system does not generate light of wavelengths, which are toxic to the eye since production of such rays is detrimental to the eye. To mitigate the detrimental effect of such rays on the eye conventional proposals require an additional light filter component to be deployed. However installation of such a filter component means that cost and maintenance of the illumination system is increased.

There is therefore a requirement in the art for an illumination system in which the wavelength characteristics of the light source used in the illumination system does not generate light of wavelengths, which are toxic to the eye since production of such rays is detrimental to the eye. The need in the art is for an illumination system, which does not require the installation of a filter component.

There is therefore a requirement in the art for an illumination system in which usage of a beam splitter component should not cause generation of secondary reflections. Such an occurrence decreases the efficiency and is detrimental to the overall outcome of the eye surgery since the surgeon is likely to be distracted due to the secondary reflections.

There is therefore a requirement in the art for an illumination system in which the mechanical components deployed for stability of the microscope are robust and the instrumentation employed by the surgeon is stable. Such an arrangement will ensure that the results of the eye surgery performed are excellent and the results are satisfactory to both the patient and the surgeon alike.

OBJECTS OF THE INVENTION

The present invention is embodied by illumination system for ophthalmic microscope, and its operation method so as to fulfill the objective(s) as enumerated and described in the present disclosure. A person skilled in the art is very well aware that the enumerated objective(s) of the system and its operation method as embodied in the present invention are merely illustrative of the scope and purview of the present invention as described in the present disclosure. However such an illustration may not be construed to restrict the present invention in any manner. It will be very clear to a person skilled in the art that any additional variation(s), functional equivalent(s) and/or any structural alternative(s) to the present invention may also be understood to be within the scope and purview of the present invention, as described in the present disclosure and also if not been explicitly stated. The present invention may be embodied in other specific forms without departing from the spirit or essential attributes thereof.

In view of the above-mentioned requirements which enable the present invention to fulfill the unmet need(s) in the art, it will be amply clear to a person skilled in the art that an objective of the present invention is to provide an illumination system for ophthalmic microscope, and its operation method in which the light source used does not generate excessive heat and is thereby conducive to eye surgery in view of the delicate internal structure of the eye and the fact that the eye is vulnerable to any excessive heat in the vicinity leading to detrimental effect on the eye while it is being operated on and also in the post-operative stage.

Yet another objective of the present invention is to provide an illumination system for ophthalmic microscope, and its operation method in which the light source used generates light of wavelengths, which are very much within the visible spectrum and are non toxic to the patient's eye, and due to which an additional light filter component is not required. As a result, cost and maintenance of the illumination system is not increased. The system also becomes more economically viable than the conventionally available systems.

Still another objective of the present invention is to provide an illumination system in which secondary reflections are not caused, which are detrimental to the overall outcome of the eye surgery. Therefore eliminating the requirement of light trap device.

Still another objective of the present invention is to provide an illumination system in which the mechanical components deployed for stability of the microscope are robust. Therefore the overall outcome of the surgery is as desired.

The present invention fulfills the above-mentioned objectives, and in the process, responds to the unmet need(s) in the art. The present invention provides a illumination system for the ophthalmic microscope and its operation method employed, in eye surgery in general, with particular focus to, cataract surgery.

SUMMARY OF THE INVENTION

The present invention as embodied by a illumination system for ophthalmic microscope and its operation method, succinctly fulfills the abovementioned objectives of the present invention, which are as broadly enumerated in the above-mentioned paragraph of the present disclosure. However it would be amply clear to a person skilled in the art that, inasmuch as the objectives that have been enumerated in the above-mentioned paragraph, such objectives are only indicative of the scope and general coverage of the present invention.

This statement of enumerated objectives should be considered as merely indicative and is no way restrictive of the scope and ambit of the present invention in its entirety. The enumerated objectives should not only be considered as indicative of the scope and ambit of the present invention, but also, any combination, variation, functional equivalent and/or any structural alternative should be construed to be within the broad scope of the present invention, even though such a scope of the present invention has not been explicitly stated herein and elsewhere in the present disclosure.

The present invention reveals illumination system for an ophthalmic microscope, and its operation method. The light source is activated, said light source producing light of wavelength, said wavelength being of non-toxic nature to the eye. The system as embodied in the present invention comprises a light source for the microscope. The light source is a Light Emitting Diode (LED). Preferably the LED used in the present invention are white light producing LEDs and the size of the chip will be greater than 1 mm. LEDs are used directly for oblique and stereo co-axial illumination and both the LEDs are capable of being individually controlled. It will be amply clear to a person skilled in the art that, the light source embodied as a white LED is for the purpose of illustration only, and may be taken to mean any light source of similar functionality and light generating property. The emitted light is then incident on virtual mirror after being incident on a condenser lens system, an aperture stop, a relay lens system and a beam splitter prism. According to the invention the illumination system of the operating microscope is constructed with a Virtual Beam Splitter (VBS) for coupling at least one illumination beam path to at least one observation beam path, an observation optical system including Objective lens opposed to an eye to be operated. An illumination system having a virtual beam splitter referred as a small mirror of size coated on a plain glass plate to reflect a beam incident on it. The purpose of the virtual beam splitter is to maximize the reflection percentage and to minimize the stray light, which will enhance the image contrast. This will eliminate the usage of light trap device used by other ophthalmic microscope system. The area of mirror coating on glass plate is determined based on uninterrupted visualization of object by observer. It is provided according to the invention that the area of the mirror coating lies in the range of 1 mm to less than the diameter of the adjacent observation lens system. It is preferably provided that the size varies from 3 to 6 mm. Virtual beam splitter (VBS) is used for obtaining an enhanced red reflex on an observation image when we place it coaxially with observation beam path. It's a special system in ophthalmic microscopes which helps to couple the Illumination beam with observation beam path. Alternatively the virtual beam splitter as embodied in the present invention comprises two very small reflective circular areas as spot, each of 3 mm diameter, which reflect most of the light, and the rest of the area of the glass plate is completely transmissive as against conventional beam splitter devices in which 50 percent of incident light is reflected and the remaining light is transmitted. Converged illumination beam deflected by this virtual mirror is incident on objective lens system and on to the anterior segment of the patient's eye and illuminates it with an intense red glow termed as "red reflex". Said lens system is a primary system common for both observation and illumination. For illumination it acts as a projection system to project the beam from the source to target plane for uniform illumination. For observation it acts as a collimator. This type of illumination is very advantageous in cataract operations, because tissue remnants, which occur upon removal of lens and are to be removed without fail to prevent complication can be effectively detected in the back lighting of the red reflex. The generation of the red reflex has become an important aid in modern operating techniques. The patient's eye illuminated by "red reflex" is viewed by the observer/eye surgeon via a observation system comprising zoom lens and a binocular lens.

BRIEF DESCRIPTION OF DRAWING

Cataract is a commonly occurring eye disorder that is curable only by surgery. Even though the outcome of the surgery is dependant on the expertise of the surgeon, it is also enhanced by the instrumentation and medication used. In this context it is observed that the generation of "red reflex" has become an important aid in cataract surgery. The following drawings illustrate the description and details of the illumination system, which is capable of generating "red reflex", and the illustrative application(s) explain in detail the working of the present invention. It will be amply clear to a person skilled in the art, that the application as disclosed in the drawings are merely illustrative of the scope of the present invention and not exhaustive of the scope of the present invention, in its entirety.

DETAILED DESCRIPTION OF DRAWING

Persons skilled in the art knows that in Cataract surgery, suction technique is the method of cutting the front capsule of the crystalline lens, which is a part of the eye along the contour thereof, inserting a suction device from the cut edge, sucking the content of the whitish crystalline lens, and implanting an Inter ocular lens (IOL) therein in place of the sucked content.

When the suction technique is performed, an operating microscope is used for observation of the enlarged view of the eye to be operated. During operation, in order to improve the visualization, an image of Transillumination produced by the scattering and reflections from the retina of the eye is widely utilized.

In particular when the position of the cut edge in the front capsule is checked in order to insert the suction device and when it is determined whether or not the content of the crystalline lens is completely sucked, the intensity of "red reflex" obtained by the illumination system used is important and is a crucial component that controls the outcome of the surgery and hence, the outcome of the surgery depends to a certain degree, on the functioning of the illumination system. The efficiency of functioning of the illumination system includes, but is not restricted to, the lighting provided to illuminate the eye lens. If the efficiency of the "Red reflex" is enhanced, it is found that, outcome of the surgery improves. Therefore, continual improvements have been made in the illumination systems available conventionally to enable effective "red reflex glow". One such conventional illumination which enables producing "red glow" is illustrated with allied description in FIG. 1.

Figure 1:
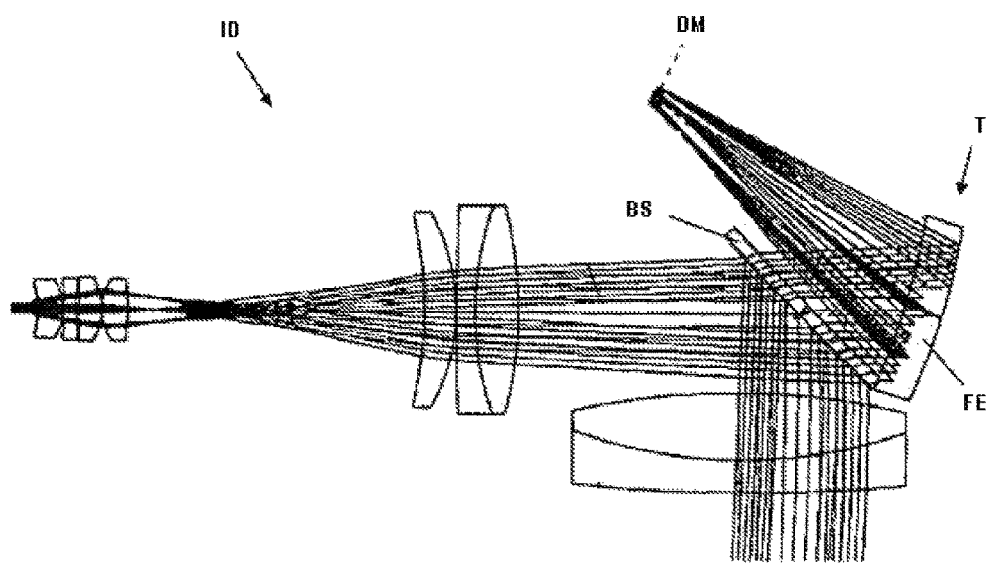
FIG. 1 illustrates the conventional illumination system.

FIG. 1 illustrates the conventional illumination system, comprising a optical fiber based light source (L) for an optical observation device is shown, which is for example, an operating microscope, e.g., for ophthalmic surgery, such as an ophthalmic microscope, a stereomicroscope in general, or similar device.

The said illumination device, provides the illumination, which illuminates the eye, on which, the "red reflex" is to be enhanced, so that, the efficiency of the surgery can be increased, thereby, enhancing the vision of the patient by replacement of the natural lens with the intra-ocular lens by way of lens transplant.

The illumination generated from the optical cable based illumination device is made to be incident on a beam-splitter (BS). The said beam splitter (BS) is coated completely with reflective material. The beam splitter transmits 50% of incident light and reflects 50% of the incident light. Said reflective material is likely to cause reflection(s) in direction(s) other than required. In order to arrest the reflection of light in direction(s) other than required, a light trap (T) device is installed.

The light trap (T) device comprises a filter element (FE) which deflects the unnecessary reflections. The light transmitted from the beam-splitter (BS) is diverged by an objective lens system, due to which the light incident on the target eye is not able to generate the "red reflex" of required intensity for successful surgery thereby, enhancing the vision of the patient.

An embodiment illustrative of the above-mentioned conventional mechanism has the deficiencies that the beam splitter element is coated completely with reflective material. This material causes generation of unnecessary reflections, thereby, decreasing the intensity of "Red reflex" generated. In order to overcome the above-mentioned deficiencies in the prior art, an illumination system of the present invention has been deployed. Said invention has been illustrated and allied description has been provided in subsequent figures.

Figure 2:
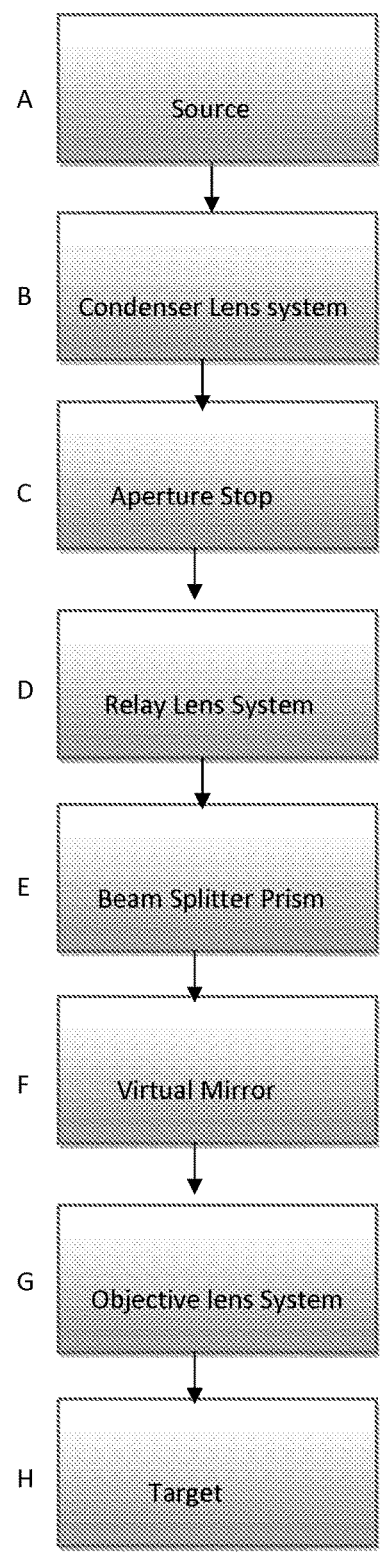
FIG. 2 illustrates the elementary flow diagram showing the components from the illumination side of the present invention.

FIG. 2 illustrates the flow diagram of illumination system of the present invention with components being depicted as blocks from the illumination side respectively.

In this context in FIG. 2, source (A) comprises two Light Emitting Diodes (LED). Preferably the LED used in the present invention are white light producing LEDs and the size of the chip will be greater than 1 mm. LEDs are used directly for oblique and stereo co-axial illumination and both the LEDs are capable of being individually controlled. The light emitted by the light source (A) is incident on condenser System (B). Aperture Stop (C) is provided to determine the area of illumination at the target area. The size of the stopper will be greater than 3 mm in diameter. Relay Lens System (D) transmits the rays from the aperture stop (C) to Beam Splitter Prism (E), which divides the convergent beam from the relay system into two beams. Said two beams are incident on Virtual Mirror (F) comprising which is selectively coated with reflector material coated on the glass plate preferably two circular areas of reflective material and then reflected back to the target area through the objective system (G). Said objective system (G) is primary system common to both observation and illumination. For illumination it acts as a projection system to project the beam from the source to target plane for uniform illumination. For Observation it acts as a collimator. Target (H) (eye on which the surgery is to be carried out) is the area where the diameter of the beam determined by the aperture stop will be focused.

Figure 3:
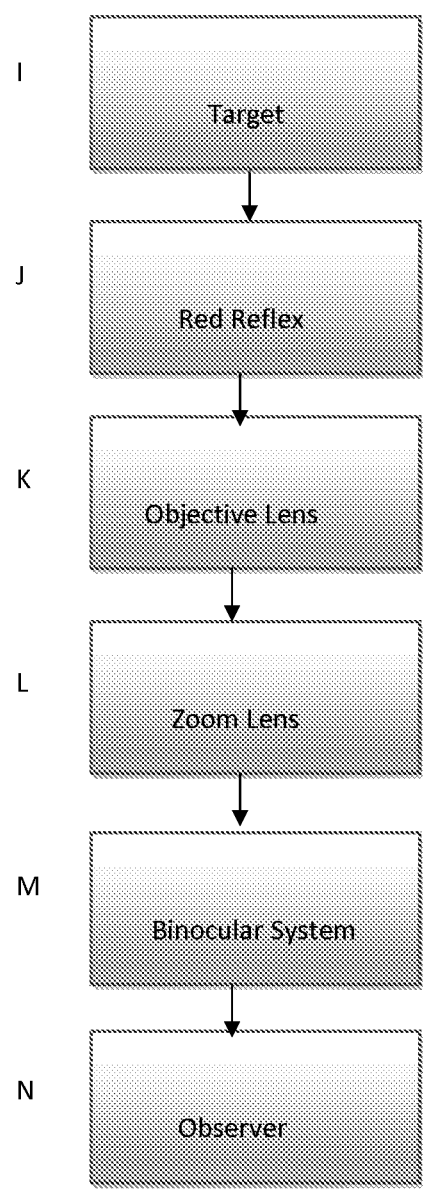
FIG. 3 illustrates the elementary flow diagram showing the components from the observation side of the present invention.

FIG. 3 illustrates the flow diagram of illumination system of the present invention with components being depicted as blocks from the observers side respectively. In FIG. 2 the incidence of the collimated beam on the eye on which surgery is to be carried out is shown (H).

Subsequently in FIG. 3, collimated beam incident on eye (I) illuminates the eye especially anterior segment of the eye which contains cornea and crystalline lens with an intense red glow termed ad red reflex (J) by people knowledgeable in the ophthalmic field. "Red Reflex" (J) is a Retinal glow generated by a stereo co-axial illumination system which aids the surgeon to perform the cataract surgery comfortably without any much difficulty. The ray from the eye (I) travels through a set of optical systems before being observed by observer/eye surgeon (N). The ray from the illuminated eye is incident on objective lens (K).

Said objective Lens (K) collimates the beam from the eye (I) and is incident on Zoom Lens System (L) of a variable magnification magnitude for microscope. Light from the zoom lens (L) is incident on binocular system (M), which is a stereo viewing device for the observer/eye surgeon (N).

Figure 4:
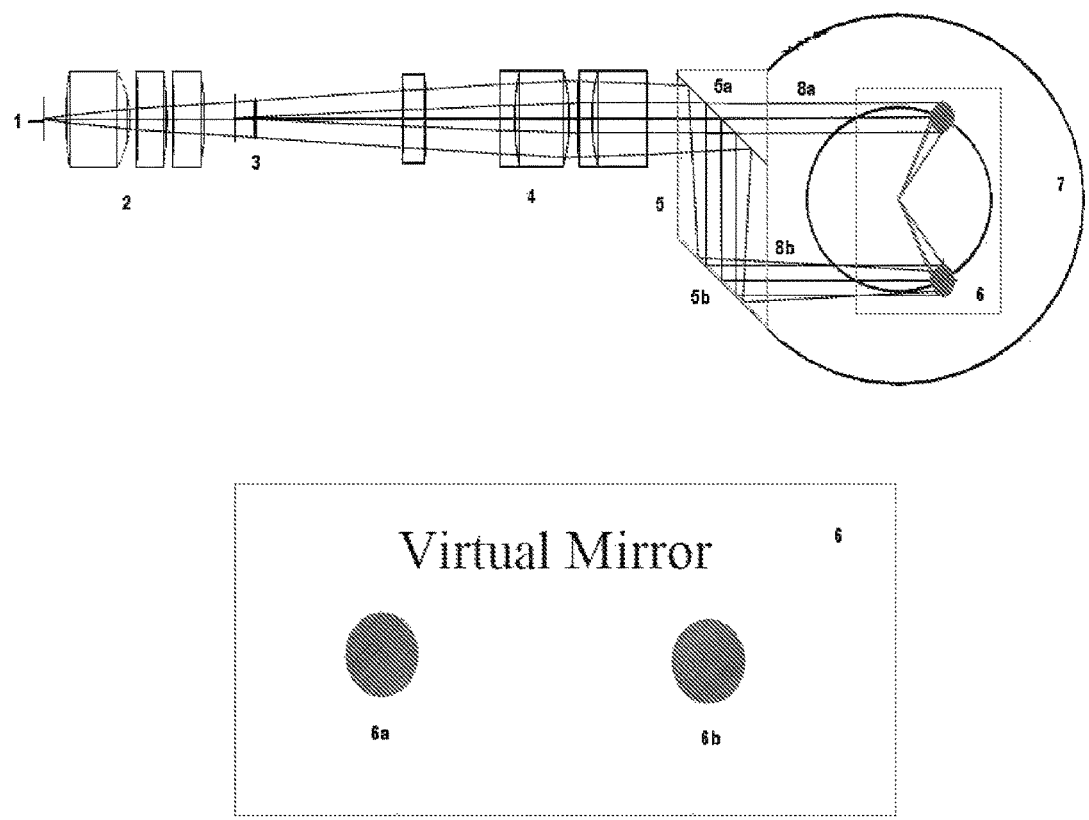
FIG. 4 illustrates the illumination system deployed in the present invention with Virtual Beam Splitter (VBS) shown in inset.

FIG. 4 illustrates the illumination system deployed in the present invention with Virtual Beam Splitter (VBS) shown in inset. The system as embodied in the present invention comprises a light source for the microscope. The light source is, a Light Emitting Diode (LED). The emitted light is then incident on virtual mirror after being incident on a condenser lens system (2), an aperture stop (3), a relay lens system (4) and a beam splitter prism (5). The system comprises a virtual beam splitter (6) for coupling at least one illumination beam path to atleast one observation beam path. An observation optical system including Objective lens is positioned opposed to an eye to be operated. As can be seen in more detail in FIG. 5, and also in inset of FIG. 4, the virtual beam splitter (6) further comprises a small mirror of size 6 mm coated on a plain glass plate to reflect the beam incident on it. Alternatively, the mirror may be two very small reflective circular areas, each of 3 mm diameter represented by reference numerals 6a and 6b. The said reflective area reflects most of the light, and the rest of the area of the glass plate is completely transmissive, as against conventional beam splitter devices in which 50 percent of incident light is reflected and the remaining light is transmitted. Illumination path is coupled to an observation beam path via virtual mirror. This will not allow the unwanted stray light beyond its position thereby preventing the use of light trap absorption material like Filter element or concave mirror behind the beam coupler. Conjugate projection system is used to illuminate the target area where the image of the source will be focused on the virtual mirror surface to reflect the beam. The beam splitter prism divides the convergent beam from the relay system (4) into two beams. The two beams from the beam splitter prism—Transmitted beams (8a) and reflected beams (8b) are made to focus on mirror coated areas (6a and 6b) of virtual beam splitter (6) which is positioned coaxially with observation system of the microscope. The reflected beam is inturn incident on the objective lens (7) and then passes to the target eye to be observed.

Figure 5:
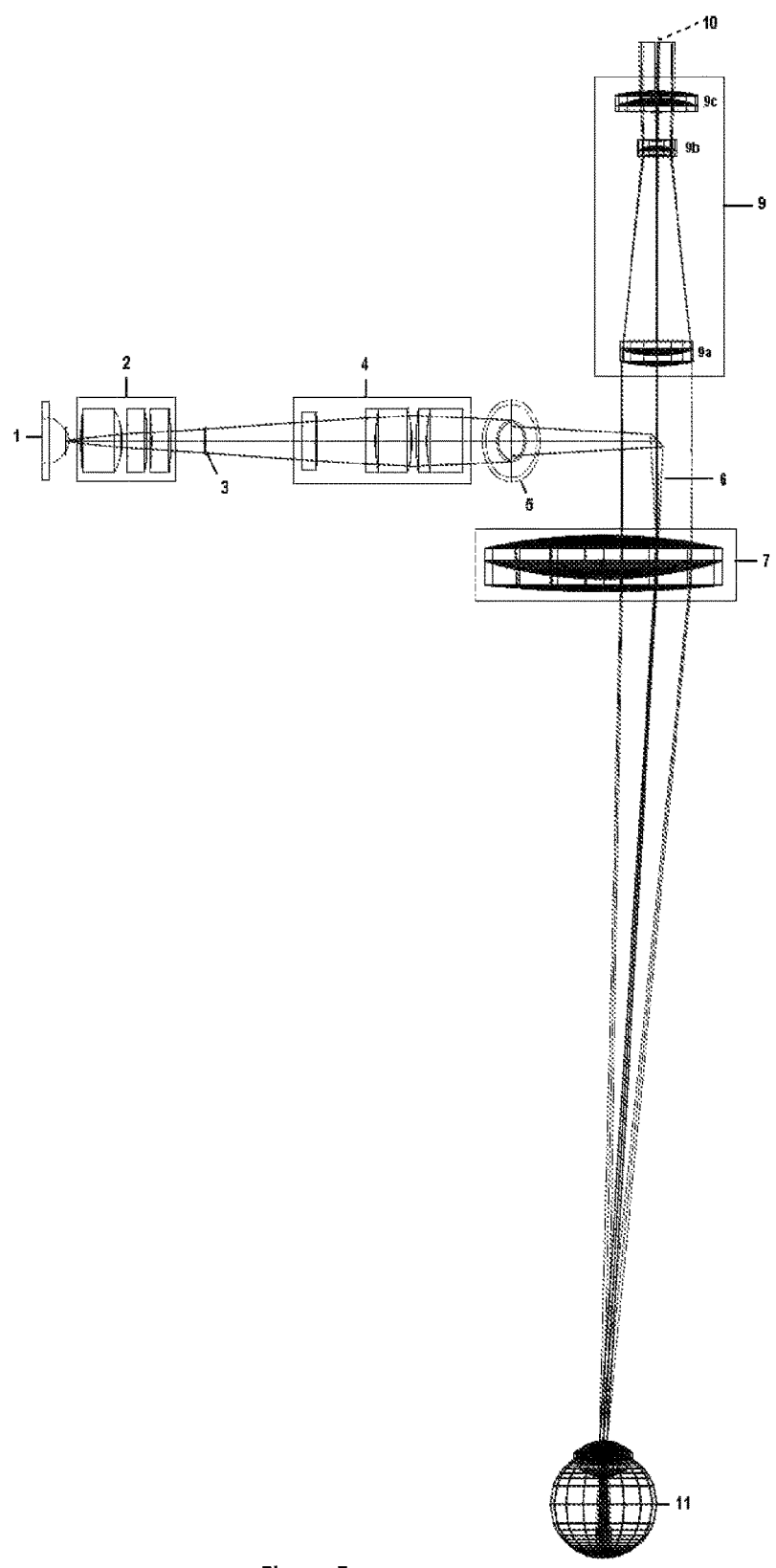
FIG. 5 illustrates the overall illumination system arrangement of the present invention

FIG. 5 illustrates the overall illumination system arrangement of the present invention.

The system as embodied in the present invention comprises a light source for the microscope. The light source is, a white Light Emitting Diode (LED) (1) used to illuminate the retina of the eye (11). It will be amply clear to a person skilled in the art that, the light source embodied as a white LED (1) is for the purpose of illustration only, and may be taken to mean any light source of similar functionality and light generating property. White LED (1) as a light source is preferred because it doesn't have any photo toxicity to cause damage to the Retina of Eye. Two LEDs each are used directly for oblique and stereo co-axial illumination and both the LED s are capable of being individually controlled.

This light beams generated from white LED then passes through the condenser (2) and relay system (4) to produce uniform illumination on retina (11) and the boundary of the illumination is determined by the aperture stop (3). Said condenser system placed next to LED collects all rays emitted from the source. Aperture stop (3) is used to determine the area of illumination at the target area i.e. eye (11) and the size of the stopper will be greater than 3 mm in diameter. The relay system (4) transmits the rays from the aperture (3) to virtual mirror (6) in terms of convergent rays.

To enhance the visualization of red glow, a single source beam is then divided into two beams using divider system (5) which contains a Beam splitter (5a) and mirror (5b) and is termed as beam splitter prism shown in detail in FIG. 4, positioned next to the relay lens (4) for stereo co-axial illumination. Conjugate projection system is used to illuminate the target area where the image of the source will be focused on the virtual mirror surface to reflect the beam. The beam splitter prism divides the convergent beam from the relay system (4) into two beams.

The two beams from the beam splitter prism-transmitted beams (8a) and reflected beams (8b) are made to focus on circular areas coated with reflective material (6a and 6b) of virtual beam splitter (6) which is positioned coaxially with observation system (9) of the microscope comprising zoom lens system (9a, 9b, 9c) and binocular lens (10), and then reflected back to the target eye area (I) through the system.

Focused beam then passes through the objective lens (7) of the microscopic system to transilluminate the human ocular system in particular retina of the eye (11). Said lens (7) is a primary system common for both observation and illumination. For illumination it acts as a projection system to project the beam from the source to target plane for uniform illumination. For observation it acts as a collimator. People knowledgeable in the ophthalmic field, understand that transillumination generally refers to the transmission of light through tissues of the body to enhance the contrast and red glow. This type of illumination is very advantageous in cataract operations, because tissue remnants, which occur upon removal of lens and are to be removed without fail to prevent complications that can be effectively detected in the back lighting of the red reflex.

Reflected beam from retina of the eye (11) then passes through the objective lens (7) and reaches the observation system (9) comprising via Virtual Beam Splitter (VBS) (6) without any visual interruption. Therefore, excellent outcome of the surgery is ensured since the outcome is not only dependant on the dexterity of the eye surgeon, but also, in the instrumentation deployed, for conducting the surgery.

The present invention has numerous advantage(s). The said advantage(s) have been enumerated in the present disclosure. It will be amply clear to a person skilled in the art that, the enumerated advantages are disclosed for the purpose of illustration only and, are provided for the purpose of indication of the advantages that are accruable by the deployment of the present invention.

The below-mentioned advantage(s) arising out of the present invention are merely indicative and are not to be considered as exhaustive of the entire advantage(s) arising by the deployment of the present invention. It will be amply clear to persons skilled in the art that, any primary advantage(s) arising out of the present invention are to be construed to be well within the scope and purview of the present invention. Further, any secondary advantage(s) arising as a result of the primary advantage(s) are also to be construed to be well within the scope and purview of the present invention.

The coupling device used in conventional illumination system is the plate beam splitter—Plane glass coated with completely reflector material. This results in stray reflections additional to the high manufacturing cost. The deployment of virtual beam-splitter with two mirror coated areas in the present invention ensures that the reflector material used is minimal, therefore, decreasing the unnecessary reflections as well as decreasing the manufacturing cost in addition to increasing the efficacy of the surgery.

Due to generation of stray reflections in case of plate beam splitter, an additional light trap device is used. Said light trap device used to capture the stray reflections in turn increases the cost. Since the present invention uses Virtual beam splitter with minimal reflector material, a light trap device is not required. This decreases the overall cost of the device.

The fiber optic cable used conventionally produces light which includes light having toxic components such as Infra red rays and ultra violet rays. In contrast the present invention uses Light Emitting Diode (LED) lamps, which ensures that, light is produced between the required wavelengths in the visual spectrum which does not have toxic components. The non-toxic nature of light produced ensures safe nature of surgery performed. In addition the fiber optic cable has a single light source as against the two LED's each for oblique and stereo co-axial illumination used in the present invention, wherein each LED can be controlled individually. The usage of fiber optic cable generates unwanted ghost images and requires a additional diaphragm to arrest unwanted ghost image at the observation path. Additional diaphragm results in increase in cost of device. In contrast the present invention uses two LED as light source and the illumination from the LED's does not generate ghost images and therefore does not require an additional diaphragm. Hence the device of the present invention is economical.

Size of the LED used is a crucial part in the process to eliminate unwanted light scatter from the co-axial reflection surface. Finite conjugate system is used for projection illumination. This path contains a beam divider prism to create co-axial beam path corresponding to the observation path coupled with illumination system. Two divided beams are then focused by the help of Objective lens at the target area. The reflection system and lenses used in the present invention ensure that the rays diverged on objective lens are converged on the eye on which the cataract surgery is to be carried out, thereby enhancing the "Red reflex" intensity causing increase in the success of the surgery.

We claim:

1. An illumination system of an ophthalmic microscope, said system comprising:
   (a) a light source, said light source comprising at least one light emitting component(s), said light emitting component(s) capable of emitting light radiation, said light radiation having a wavelength in the visible spectrum that is non-toxic to the eye of the patient;
   (b) a condenser lens system, said condenser lens system is positioned to receive the light radiation emitted from said light source;
   (c) an aperture stop positioned downstream of said condenser lens system, said aperture stop determines an area of illumination at a target site;
   (d) a relay lens system positioned downstream of said aperture stop, said relay lens system transmits light rays from said aperture stop to a beam splitter prism positioned downstream of said relay lens system;
   (e) said beam splitter prism divides a convergent beam from said relay lens system into plurality of beams;
   (f), a beam splitter positioned downstream of said beam splitter prism, said beam splitter being selectively coated with reflective material; and
   (g) an observation system.

2. The illumination system of an ophthalmic microscope as claimed in claim 1, wherein the light emitting component is an LED.

3. The illumination system of an ophthalmic microscope as claimed in claim 1, wherein the light emitting component is an LED emitting white light.

4. The illumination system of an ophthalmic microscope as claimed in claim 1, wherein the beam splitter being a plane glass plate selectively coated with the reflective material.

5. The illumination system of an ophthalmic microscope as claimed in claim 1, wherein the beam splitter being selectively coated with reflective material includes two circular areas of reflective material.

6. A method of operation of an illumination system of an ophthalmic microscope, said method comprising the steps of:
   (a) activating a light source, said light source producing light of a wavelength, said wavelength is in the visible spectrum that is non-toxic to the eye;
   (b) causing emitted light to be incident on a virtual mirror after being incident on a condenser lens system, an aperture stop, a relay lens system and a beam splitter prism;
   (c) causing light incident on the virtual mirror to be converged on the eye, said convergence causing illumination of the eye;
   (d) causing light reflected from the eye to be incident on an objective lens system;
   (e) enabling the observer to view the illuminated eye via an observation system.

7. The method of operation of the illumination system of an ophthalmic microscope as claimed in claim 6, wherein the light source is at least one light emitting diode.

8. The method of operation of the illumination system of an ophthalmic microscope as claimed in claim 7, wherein the light emitting diode emits white light.

9. The method of operation of the illumination system of an ophthalmic microscope as claimed in claim 6, wherein the virtual mirror being a plane glass plate selectively coated with reflective material including at least an area of reflective material.

10. The method of operation of the illumination system of an ophthalmic microscope as claimed in claim 6, wherein the virtual mirror comprises a plane glass, said plane glass being selectively coated with reflective material including two circular areas of reflective material.

* * * * *